(12) United States Patent
Himmelreich et al.

(10) Patent No.: US 8,778,842 B2
(45) Date of Patent: Jul. 15, 2014

(54) SAMPLE LYSIS AND COATING OF REACTION SURFACE

(75) Inventors: Ralf Himmelreich, Langenfeld (DE); Roland Fabis, Köln (DE); Christoph Erbacher, Haan (DE); Sabine Werner, Düsseldorf (DE); Bernd Springer, Wülfrath (DE)

(73) Assignee: QIAGEN GmbH, Hilden (DE)

( * ) Notice: Subject to any disclaimer, the term of this patent is extended or adjusted under 35 U.S.C. 154(b) by 998 days.

(21) Appl. No.: 11/883,071

(22) PCT Filed: Feb. 6, 2006

(86) PCT No.: PCT/EP2006/001019
§ 371 (c)(1),
(2), (4) Date: Mar. 25, 2008

(87) PCT Pub. No.: WO2006/084650
PCT Pub. Date: Aug. 17, 2006

(65) Prior Publication Data
US 2008/0299557 A1   Dec. 4, 2008

Related U.S. Application Data

(60) Provisional application No. 60/652,114, filed on Feb. 10, 2005.

(51) Int. Cl.
*C12Q 1/68* (2006.01)
*C08G 73/02* (2006.01)

(52) U.S. Cl.
USPC ............... 506/4; 506/6; 528/422; 528/332

(58) Field of Classification Search
CPC .................................. C12Q 1/68; C08G 73/02
USPC .................................. 435/6, 4; 528/422, 332
See application file for complete search history.

(56) References Cited

U.S. PATENT DOCUMENTS

| | | | |
|---|---|---|---|
| 3,192,066 A | 6/1965 | Raes | 117/145 |
| 4,085,057 A | 4/1978 | Masuda et al. | 252/62.1 |
| 4,378,803 A | 4/1983 | Takagi et al. | 604/280 |
| 4,780,228 A | 10/1988 | Gardiner et al. | 252/51 |
| 6,469,081 B1 | 10/2002 | Chino et al. | 524/261 |
| 6,492,455 B1 * | 12/2002 | Nadolsky | 524/559 |
| 7,200,088 B2 * | 4/2007 | Worthington et al. | 369/53.31 |
| 2002/0009659 A1 | 1/2002 | Ebisu et al. | 430/45 |
| 2002/0168652 A1 | 11/2002 | Werner et al. | 435/6 |
| 2003/0003455 A1 | 1/2003 | Rundell et al. | 435/6 |
| 2003/0124029 A1 | 7/2003 | Webb et al. | 422/102 |
| 2003/0147958 A1 | 8/2003 | Ahn et al. | 424/486 |
| 2004/0012839 A1 | 1/2004 | Cao et al. | 359/296 |
| 2004/0087720 A1 | 5/2004 | Delius et al. | 525/66 |
| 2004/0121334 A1 * | 6/2004 | Wei et al. | 435/6 |

FOREIGN PATENT DOCUMENTS

| | | | |
|---|---|---|---|
| EP | 0228225 A2 * | 12/1986 | |
| EP | 0 395 279 A1 | 10/1990 | |
| JP | 59-174620 A | 10/1984 | |
| WO | 99/60051 A2 | 11/1999 | |

* cited by examiner

*Primary Examiner* — Maria Leavitt
*Assistant Examiner* — Amy M Bunker
(74) *Attorney, Agent, or Firm* — Seed IP Law Group PLLC

(57) ABSTRACT

The present invention provides copolymers that facilitate nucleic acid analysis, compositions that comprise such copolymers, and methods for making or using such copolymers.

31 Claims, 4 Drawing Sheets

SAMPLE LYSIS AND COATING OF REACTION SURFACE

BACKGROUND OF THE INVENTION

1. Field of the Invention

The present invention relates to copolymers that facilitate nucleic acid analysis.

2. Description of the Related Art

Immobilizing nucleic acid molecules on a solid surface facilitates nucleic acid preparation and analysis, especially in a high throughput format. An exemplary nucleic acid preparation and analysis system is the Direct Plate Prep system in which the lysis of blood takes place in a PCR plate coated with a DNA binding polymer. The DNA extracted from the blood binds to the polymer on the plate. The plate can then be washed, and PCR can be initiated by adding the necessary ingredients for the reaction. A similar product was available from Trinity Biotech PLC. The so-called "Xtra-Amp Plates" are coated with silica, and the lysis of a biological sample and binding of the nucleic acid extracted from the sample to the coated plate may be performed by the use of chaotropic salts.

As described above, the presently available nucleic acid preparation and analysis systems require that the vessels where nucleic acid extraction and/or analysis takes place be pre-coated with a DNA binding polymer. Accordingly, there is a need in developing simpler and/or more efficient systems.

BRIEF SUMMARY OF THE INVENTION

The present invention provides copolymers that facilitate nucleic acid analysis, compositions that comprise such copolymers, and methods for making and using such copolymers.

In one aspect, the present invention provides a copolymer comprising a moiety obtainable from a first component, a moiety obtainable from a second component and a moiety obtainable from a component containing an amino group, wherein the first component comprises a hydrophobic monomer or a derivative thereof, the second component comprises a monomer or a derivative thereof providing at least one functionality to which the component containing an amino group may be directly or indirectly linked and wherein the component containing the amino group is directly or indirectly covalently linked to the second component.

In case the component containing an amino group is linked indirectly to the second component it is preferred that the second component is covalently linked to one end of a spacer and another end of the spacer is linked to the component containing an amino group.

It is as well possible to use a mixture of two or more different monomers as the first component and a mixture of two or more monomers as the second component.

In a further embodiment the moiety obtainable from the first component comprises a first hydrophobic polymer or a derivative thereof, the moiety obtainable from the second component comprises a second polymer or a derivative thereof, and the moiety obtainable from the component containing an amino group is covalently linked to the second component. Such an embodiment may be formed in case the monomer of the first component forms a polymer and the monomer of the second component forms a polymer and the resulting polymers are linked to each other. This may be the case, for example, in block copolymers or graft polymers.

The moiety resulting from the hydrophobic monomers or the resulting hydrophobic polymer moiety, respectively, allow the copolymer to form a film on a hydrophobic surface whereas the moiety resulting from the second monomers or the second polymer moiety, respectively, provide a functionality so that a component containing an amino group may be directly or indirectly attached to the copolymer. The amino group in turn provides a positive charge to allow the copolymer to bind nucleic acid molecules. In other words, the copolymer of the present invention is capable of immobilizing nucleic acid molecules on a hydrophobic surface by the hydrophobic interaction between the moiety resulting from the hydrophobic monomers or the hydrophobic polymer component, respectively, and the hydrophobic surface and by the electrostatic interaction between its positively charged amino group and the negatively charged nucleic acid molecules.

Exemplary copolymers of the present invention include, but are not limited to, amino-modified poly(styrene-co-maleic acid anhydride), amino-modified poly(isoprene-graft-maleic acid anhydride), amino-modified poly(methylvinylether-alt-maleic acid anhydride), amino-modified stearyl acrylate-glycidyl methacrylate copolymer, and amino-modified poly(styrene-glycidyl methacrylate) copolymer.

In another aspect, the present invention provides compositions that comprise the copolymers described herein, such as copolymer-containing lysis buffers.

In another aspect, the present invention provides complexes formed by interaction between the copolymers described herein and nucleic acid molecules.

In another aspect, the present invention provides kits for performing biological assays that comprise the copolymers described herein. Exemplary kits include, but are not limited to, kits for sample preparation that comprise the copolymers of the present invention and lysis buffers, kits for nucleic acid amplification that comprise the copolymers of the present invention, lysis buffers, optionally wash buffers, DNA polymerases, and dNTPs.

In another aspect, the present invention provides vessels for performing nucleic acid assays that are coated with the copolymers described herein.

In another aspect, the present invention provides methods for extracting nucleic acid from biological samples that comprise mixing nucleic acid-containing biological samples with lysis buffers that comprise the copolymers described herein.

In another aspect, the present invention provides methods for immobilizing nucleic acid to hydrophobic surfaces that comprise simultaneously or sequentially applying the copolymers described herein and nucleic acid to hydrophobic surfaces.

In another aspect, the present invention provides methods for nucleic acid amplification that comprise (i) combining a nucleic acid-containing biological sample with a copolymer-containing lysis buffer, (ii) applying the mixture formed in step (i) to a hydrophobic surface so that the nucleic acid in the biological sample is immobilized on the hydrophobic surface with the copolymer in the lysis buffer, and (iii) performing nucleic acid amplification using the nucleic acid immobilized on the hydrophobic surface as a template.

DETAILED DESCRIPTION OF THE INVENTION

Figure 1:
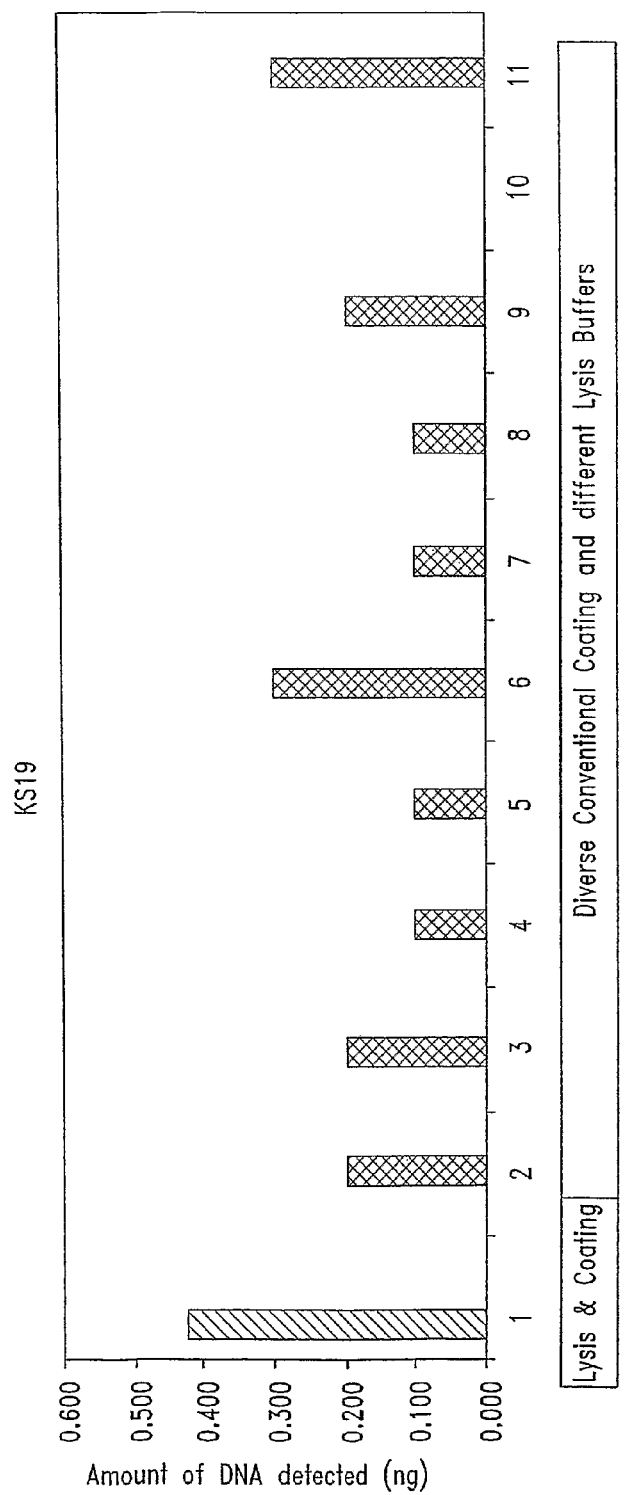
FIG. 1 is a bar graph showing the results of quantitative real time PCR that amplified beta-actin. The y-axis displays the amount of DNA detected in nanogram. The x-axis indicates different preparation setups using different lysis buffers.

The present invention provides copolymers that facilitate nucleic acid analysis, compositions that comprise such copolymers, and methods for making and using such copolymers.

In one aspect, the present invention provides a copolymer capable of binding to both a hydrophobic surface and nucleic acid molecules. More specifically, the copolymer of the present invention comprises a moiety obtainable from a first component, a moiety obtainable from a second component, and moiety obtainable from a component containing an amino group. The first component comprises a hydrophobic monomer moiety or its derivative any may lead to a polymer moiety, which allows the copolymer to bind to a hydrophobic surface via hydrophobic interactions. The second component comprises a second monomer moiety or a derivative thereof, and may lead to a second polymer moiety, which provides a reactive group that allows the attachment of a compound containing an amino group to the copolymer either directly or indirectly.

The monomers of the first component may comprise any hydrophobic monomer or derivatives thereof. Such hydrophobic monomers can be exemplified by unsaturated aromatics like styrene, alkenes like ethylene or propylene or by alkapolyenes (polyenes) like butadiene.

In case the monomers of the first component result in a polymer the copolymer comprises a first component which may comprise any hydrophobic polymers or derivatives thereof. Exemplary hydrophobic polymers include, but are not limited to, polystyrene, polyalkenes like polyethylene or polypropylene and polyalkapolyenes like polybutadiene.

The second component may comprise any monomers or may result in any polymers or derivatives thereof that contain a reactive group to allow attachment of compound containing an amino group directly (i.e., via a reaction directly with an amino group-containing compound) or indirectly (i.e., via one or more reactions with compound(s) that do not contain an amino group first wherein at least a portion of those compound(s) is incorporated into the final copolymer product and such portion provides for further attachment of an amino group-containing compound). In certain embodiments, the second component comprises an amine reactive group. In certain other embodiments, the second component comprises a hydroxyl reactive group. Exemplary reactive groups include, but are not limited to, a carboxylate, an anhydride, an aldehyde and an epoxide group. The monomers of the second component can be exemplified by maleic anhydride, acrylic acid, 4-hydroxystyrene, 4-vinyl-benzaldehyde and derivatives thereof. In case the monomers of the second component form second component polymers exemplary second components include, but are not limited to, poly(maleic anhydride), poly(acrylic acid), poly(methacrylic acid), poly(4-hydroxystyrene), poly(4-vinyl-benzaldehyde), and derivatives of the above-listed polymers.

In certain embodiments, the copolymer of the present invention may be synthesized by modifying a copolymer that is obtainable from polymerization of hydrophobic monomers and monomers providing at least one functionality to which a component containing an amino group may be linked or by modifying a copolymer that comprises a hydrophobic polymer and another polymer with a compound carrying an amino group (e.g., a primary, secondary, or tertiary amine). The compound carrying an amino group may further comprise a second functional group, such as another amino group or a hydroxyl group to interact with a reactive group on the copolymer. Exemplary compounds carrying an amino group include, but are not limited to, 2-(diisopropylamino)-ethylamine, N,N-diethyldiethylenetriamine, 1-(2-aminoethyl)pyrrolidine, 1-amino-4-methylpiperazine, N,N,2,2,-tetramethyl-1,3,-propanediamine, 3-(dibutylamine)propylamine, Girard's reagent T, choline chloride, 2-(2-diethylaminoethylamino)-ethanol, 2-{[2-(dimethylamino)ethyl]methylamino]ethanol, 1,3-bis-(diethylamino)-2-propanol, a-(diisopropylamino)ethanol, 2-[2-(dimethylamino)ethoxy]ethanol, 4-diisobutylamino-1-butanol, 6-dipropylamino-1-hexanol, or diethanolamine.

In certain embodiments, the second component may further comprise a spacer portion that links a monomer of the second component or of the second polymer to the component containing an amino group. The spacer portion allows optimization of the distance between the amino group and the hydrophobic polymer backbone, and thus optimization of nucleic acid immobilization onto a hydrophobic surface.

The spacer portion may be derived from a spacer-forming molecule that reacts with a copolymer comprising the first and second components either before or at the same time as the copolymer reacts with an amino group-containing compound. Spacer-forming molecules may be any molecules capable of reacting with both a reactive group of the moiety obtained from the second monomers or the polymer moiety of the second component, respectively, and another reactive group of an amino group-containing compound. Exemplary spacer-forming molecules include, but are limited to, lactono-lactone, unmodified and chemically modified poly(ethylene glycol) with the general formula HO—$(C_2H_4O)_n$—H wherein n is 1 to 20,000, unmodified and chemically modified poly(propylene glycol) with the general formula HO—$(C_3H_6O)_m$—H wherein m is 1 to 20,000, glycerol diglycidylether, glycerol-propoxylate triglycerolether, and poly(meth)acrylic acid.

The copolymers of the present invention may be block polymers, graft polymers, statistical polymers or alternative polymers. They can be linear or branched.

Exemplary copolymers of the present invention include, but are not limited to, amino-modified poly(styrene-co-maleic anhydride), amino-modified poly(isoprene-graft-maleic anhydride), amino-modified poly(methylvinylether-alt-maleic anhydride), amino-modified stearyl acrylate-glycidyl methacrylate copolymer, and amino-modified poly(styrene-glycidyl methacrylate) copolymer.

The copolymers of the present invention may contain from about 5% to about 60% (weight percentage, including any value within this range) of the monomers of the second component. For instance, amino-modified poly(styrene-co-maleic anhydride), amino-modified poly(isoprene-graft-maleic anhydride), and amino-modified poly(methylether-alt-maleic anhydride) may each contain about 7% to about 50% (weight percentage, including any value within this range) of maleic anhydride.

The copolymers of the present application may be synthesized by first synthesizing, or otherwise obtaining, a copolymer obtainable from a first hydrophobic monomer and a second monomer having the above specified functionality or by first synthesizing a copolymer that comprises a hydrophobic polymer and a second polymer, and then modifying the resulting copolymer directly or indirectly with an amino group-containing compound. For example, poly(styrene-co-maleic anhydride) copolymer is commercially available and may be covalently coupled with 2-diisopropylamino-ethylamine (DIPAEA) via aminolysis. Example 1 below provides such exemplary synthesis schemes.

As described above, the copolymers of the present invention facilitate nucleic acid immobilization and analysis. For instance, the copolymers of the present invention may be included in a lysis buffer or another nucleic acid extraction or preparation buffer. The resulting buffer may be combined with a biological sample and subsequently added to a reaction vessel with a hydrophobic surface. The copolymer in the buffer forms a film on the hydrophobic surface of the reaction vessel via its single hydrophobic moieties or its hydrophobic polymer moiety whereas its amino group binds to nucleic acid molecules. The nucleic acid molecules immobilized to the hydrophobic surface may then be amplified and/or analyzed. Thus, the inclusion of the copolymers of the present invention allows the combination of sample lysis and reaction vessel coating and consequently simplification of nucleic acid analysis.

Alternatively, the copolymer-containing buffer as described above may be first added to, and thus coat, a reaction vessel. A biological sample may be then added to the buffer in the coated reaction vessel.

Biological samples that may be analyzed by the methods according to the present invention include any samples that potentially contain nucleic acid molecules. Such samples may be directly isolated from an organism, or may be subsequently processed. Exemplary biological samples include, but are not limited to, blood, body fluids, and cultured cells.

The copolymers of the present invention preferably do not interfere with assays performed on the nucleic acid molecules to which the copolymers bind. Such assays include nucleic acid hybridization and nucleic acid amplification, such as various types of PCR.

Accordingly, in one aspect, the present invention provides compositions that comprise the copolymers described herein, such as copolymer-containing lysis buffers. In another related aspect, the present invention provides complexes formed by interaction between the copolymers described herein and nucleic acid molecules.

In another related aspect, the present invention provides kits for performing biological assays that comprise the copolymers described herein. Exemplary kits include, but are not limited to, kits for sample preparation that comprise the copolymers of the present invention and lysis buffers and kits for nucleic acid amplification that comprise the copolymers of the present invention, lysis buffers, optionally wash buffers, DNA polymerases, and dNTPs.

In another aspect, the present invention provides vessels for performing nucleic acid assays that are coated with the copolymers described herein. Exemplary vessels that may be coated include, but are not limited to, multi-well plates or strips for performing PCR and PCR tubes. In a related aspect, the present invention provides solid substrates for binding and analyzing nucleic acid. Such substrates include, but are not limited to, slides and chips that may be used in binding nucleic acid and performing hybridization assays or other nucleic acid analysis.

In another aspect, the present invention provides methods for extracting nucleic acid from biological samples that comprise mixing nucleic acid-containing biological samples with lysis buffers that comprise the copolymers described herein. Such methods may further comprise adding the resulting mixture to a reaction vessel with a hydrophobic surface.

In another aspect, the present invention provides methods for immobilizing nucleic acid to hydrophobic surfaces that comprise simultaneously or sequentially applying the copolymers described herein and nucleic acid to hydrophobic surfaces. In the embodiments where the nucleic acid and the copolymer are simultaneously applied to a hydrophobic surface, the nucleic acid may be combined with the copolymer before the application, or the nucleic acid and the copolymer may be separately applied to the surface.

In another aspect, the present invention provides methods for nucleic acid amplification that comprise (i) combining a nucleic acid-containing biological sample with a copolymer-containing lysis buffer, (ii) applying the mixture formed in step (i) to a hydrophobic surface so that the nucleic acid in the biological sample is immobilized on the hydrophobic surface with the copolymer in the lysis buffer, and (iii) performing nucleic acid amplification using the nucleic acid immobilized on the hydrophobic surface as a template. These methods may further comprise washing the hydrophobic surface before step (iii) with a wash buffer.

An exemplary method according to the present invention comprises: (i) combining a blood sample with an erythrocyte lysis buffer that contain poly(styrene-co-maleic anhydride) covalently coupled with DIPAEA to form a mixture; (ii) adding the mixture of step (i) to a reaction vessel with a hydrophobic surface (e.g., PCR plates or strips); (iii) removing the solution in the reaction vessel; (iv) optionally washing the reaction vessel with a wash buffer; (v) performing PCR in the reaction vessel; and (vi) optionally detecting amplified nucleic acid molecules.

In case the copolymer is formed of first and second polymers a further group of embodiments can be summarized as follows:

1. A copolymer comprising a first component, a second component, and an amino group, wherein (i) the first component comprises a first hydrophobic polymer or a derivative thereof, (ii) the second component comprise a second polymer or a derivative thereof, and (iii) the amino group is covalently linked to the second component.

2. The copolymer of 1 wherein the first hydrophobic polymer is polystyrene.

3. The copolymer of 1 wherein the first hydrophobic polymer is polyethylene, polypropylene, polybutadiene, polyalkene, or polyalkapolyene.

4. The copolymer of 1 wherein the second polymer is poly(maleic anhydride), poly(acrylic acid), or poly(methacrylic acid).

5. The copolymer of 1 wherein the second polymer is poly(4-hydroxy-styrene), poly(4-vinyl-benzaldehyde), or a derivative thereof.

6. The copolymer of 1 wherein the second component further comprises an amine reactive group.

7. The copolymer of 6 wherein the amine reactive group is a carboxylate, aldehyde, or epoxide group.

8. The copolymer of 1 wherein the second component further comprises a hydroxyl reactive group.

9. The copolymer of 1 wherein the amino group is covalently linked to the second component by modifying a copolymer comprising the first hydrophilic polymer and the second polymer with a compound carrying an amino group.

10. The copolymer of 9 wherein the compound carrying an amino group is a primary, secondary, or tertiary amine.

11. The copolymer of 9 wherein the compound carrying an amino group further comprises a second amino group.

12. The copolymer of 9 wherein the compound carrying an amino group further comprises a hydroxyl group.

13. The copolymer of 9 wherein the compound carrying an amino group is 2-(diisopropylamino)-ethylamine, N,N-diethyldiethylenetriamine, 1-(2-aminoethyl)pyrrolidine, 1-amino-4-methylpiperazine, N,N,2,2,-tetramethyl-1,3,-propanediamine, 3-(dibutylamine)propylamine, Girard's reagent T, choline chloride, 2-(2-diethylaminoethylamino)-ethanol, 2-{[2-(dimethylamino)ethyl]methylamino}ethanol, 1,3-bis-(diethylamino)-2-propanol, a-(diisopropylamino) ethanol, 2-[2-(dimethylamino)ethoxy]ethanol, 4-diisobytylamino-1-butanol, 6-dipropylamino-1-hexanol, or diethanolamine.

14. The copolymer of 1 wherein the second component further comprises a spacer portion that links a monomer of the second polymer to the amino group.

15. The copolymer of 1 wherein the spacer portion is derived from a spacer-forming molecule selected from the group consisting of lactonolactone, unmodified and chemically modified poly(ethylene glycol) with the general formula HO—$(C_2H_4O)_n$—H wherein n is 1 to 20,000, unmodified and chemically modified poly(propylene glycol) with the general formula HO—$(C_3H_6O)_m$—H wherein m is 1 to 20,000, glycerol diglycidylether, glycerol-propoxylate triglycerolether, and poly(meth)acrylic acid.

16. Amino-modified poly(styrene-co-maleic acid anhydride) having about 7% to about 50% (weight percentage) maleic acid anhydride.

17. Amino-modified poly(isoprene-graft-maleic acid anhydride) having about 7% to 50% of maleic acid anhydride.

18. Amino-modified poly(methyvinyllether-alt-maleic acid anhydride) with about 50% of maleic acid anhydride.

19. Amino-modified stearyl acrylate-glycidyl methacrylate copolymer.

20. Amino-modified poly(styrene-glycidyl methacrylate) copolymer.

21. A copolymer modified by an amine, wherein the copolymer is poly(styrene-co-maleic acid anhydride), poly(isoprene-graft-maleic acid anhydride), poly(methylvinylether-alt-maleic acid anhydride), steary acrylate-glycidyl methacrylate copolymer, or polystyrene-glycidyl methacrylate copolymer, and the amine is a primary, secondary or tertiary amine.

22. A lysis buffer comprising the copolymer of any one of claims 1-21.

23. A complex comprising the copolymer of any one of claims 1-21 and a nucleic acid molecule.

24. A kit for performing a biological assay comprising the copolymer of any one of claims 1-21 and a lysis buffer.

25. A kit for performing nucleic acid amplification comprising the copolymer of any one of claims 1-21, a lysis buffer, a wash buffer, a DNA polymerase, and dNTPs.

26. A vessel for performing a nucleic acid assay coated with the copolymer of any one of claims 1-21.

27. A method for extracting nucleic acid from a biological sample comprising mixing a nucleic acid-containing biological sample with the lysis buffer of 22.

28. A method for immobilizing nucleic acid to a hydrophobic surface comprising simultaneously or sequentially applying the copolymer of any one of claims 1-21 and nucleic acid to the hydrophobic surface.

29. A method for amplifying nucleic acid comprising:
(i) combining a nucleic acid-containing biological sample with the lysis buffer of 22 to form a mixture;
(ii) applying the mixture of step (i) to a hydrophobic surface so that the nucleic acid in the biological sample is immobilized on the hydrophobic surface via the copolymer in the lysis buffer; and
(iii) performing nucleic acid amplification using the nucleic acid immobilized on the hydrophobic surface as a template.

30. The method of 29 further comprising washing the hydrophobic surface before step (iii).

The following examples are provided for illustration, not as limitations.

EXAMPLES

Example 1

Synthesis of Poly(styrene-co-maleic anhydride) Covalent Coupling with DIPAEA Via Ammonolysis Poly(styrene-co-maleic anhydride) covalent coupling With DIPAEA was synthesized as follows:
Step I. Synthesis of Lactonolacton
Regents
The following reagents were used: potassium hydroxide; methanol; Millipore water; lactose monohydrat (360.3 g/mol) (Fluka 61340); iodine (126.9 g/mol) (Fluka 57655); diethyl ether; and amberlite IR-120 (Fluka 06428).

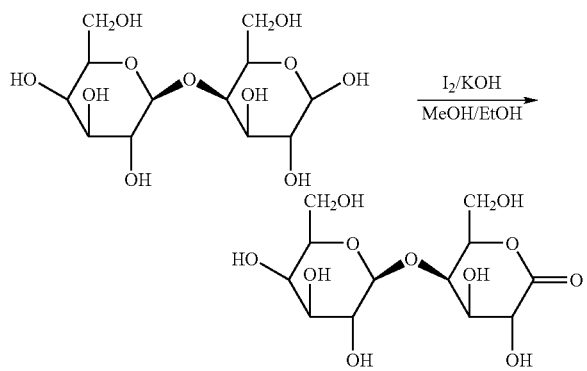

Reaction Scheme

Procedures 32 g potassium hydroxide was dissolved in 400 ml methanol. In addition, 24 g (67 mmol) lactose monohydrate was dissolved in a mixture consisting of 20 ml Millipore water and 50 ml methanol. In a three-neck flask equipped with a KPG stirrer, dropping funnel and reflux condenser, 34.2 g (270 mmol) iodine was dissolved in 240 ml methanol, and the reaction mixture was heated up to 40° C. The lactose monohydrate solution was added slowly via dropping funnel. In the next step, the dropping funnel was replaced with a new dropping funnel, and the potassium hydroxide solution was added slowly for one hour, while the reaction temperature was still maintained at 40° C. After the disappearance of the iodine color, the temperature was hold at 40° C. for another hour. The reaction mixture was cooled to 0° C. for more than 30 minutes, and the suspension was suction-filtrated through a glass suction filter, porosity 4 (Schott AG, Mainz, Germany). The residue was washed by 50 ml methanol and 50 ml diethyl ether, both cooled to 0° C., and suction filtrated to the dry state.

Then the substance was dissolved in a small amount of water and the solution was transferred to a cation exchanger column. The column was washed with Millipore water and the eluates were collected until their pH became neutral. After that, the column was washed with 500 ml Millipore water, and the eluates were pooled. In the next step, the solution was extracted twice with 250 ml diethyl ether to remove residual iodine. Then water was removed by vacuum distillation on a Rotavapor up to a volume of 50 ml. The residual water was removed by freeze-drying.

Step II. Synthesis of Poly (styrene-co-maleic anhydride) Covalent Coupling with DIPAEA via Aminolysis ("KS19" Copolymer)

Reagents

The following reagents were used: poly(styrene-co-maleic acid anhydride), alfa-cumyl-end groups, MW1600, Aldrich, Cat. No. 44,238-0; 1,6-diamino hexane, 116.2 g/mol, Fluka 33000; lactonolactone (synthesized as described above); sodium periodate; 2-(diisopropylamino)-ethylamine (DIPAEA), Fluka, Cat. No. 38320; sodium cyanoborhydride; and absolute ethanol.

Reaction Scheme

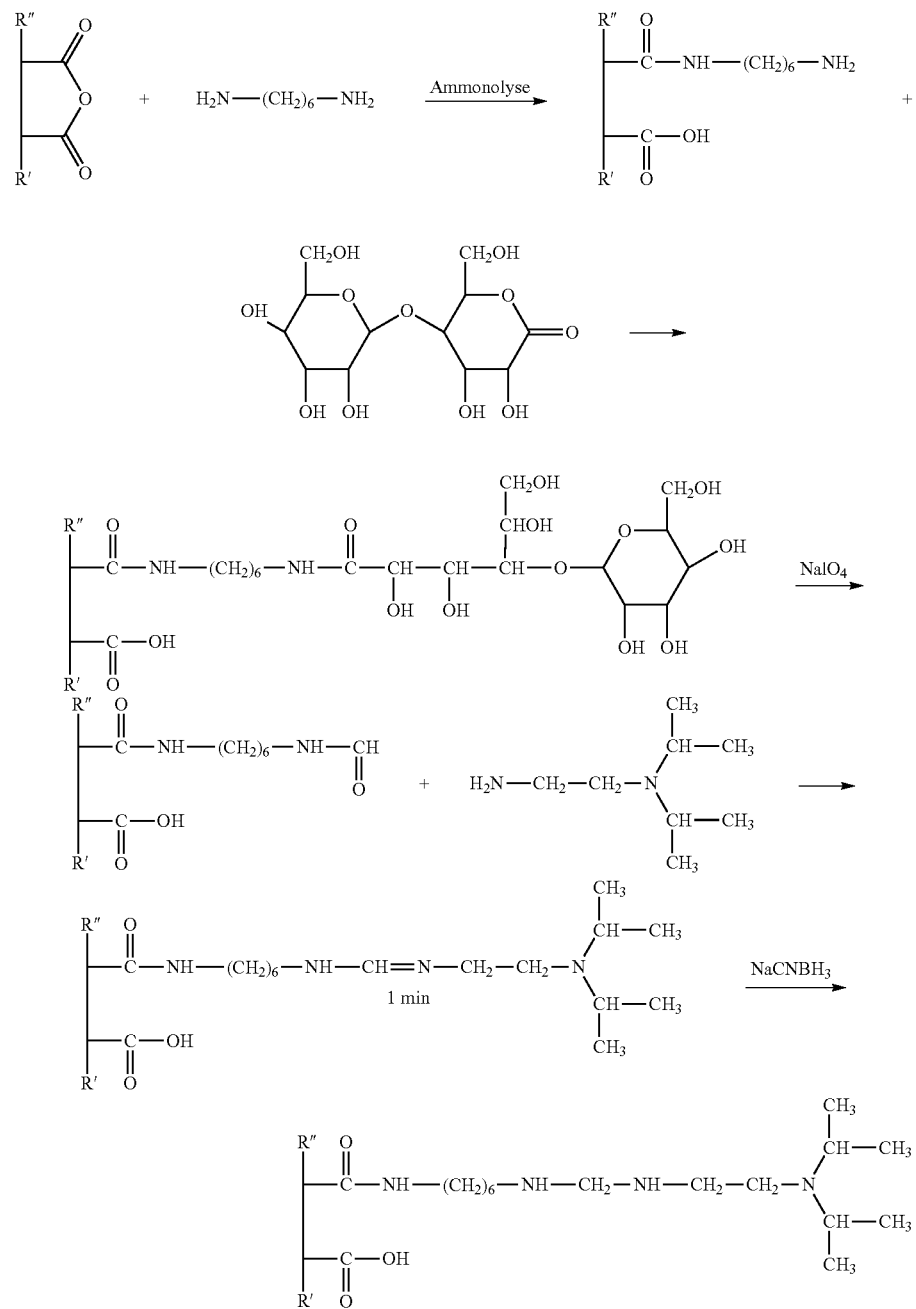

Procedure:

2.5 g of polystyrene-co-maleic anhydride was added to a 50 ml single neck flask, and 20 ml previously molten 1,6-diamino hexane was also added. The flask was attached to a Rotavapor, and the suspension was heated for one hour to 100° C., and for two more hours to 120° C. Then volatile compounds were removed at 50° C. with a reduced pressure of 1 mbar.

21.95 g of the thus obtained amino-functionalized copolymer and 2.55 g lactonolactone were added to a mortar and were mixed by grinding. The mixture was then added to 50 ml Millipore water in a 100 ml single-neck flask, and then heated to 75° C. for six hours. Then the reaction mixture was concentrated to the dry state under reduced pressure on a Rotavapor.

1000 mg of this copolymer-lactonolacton-addition compound were added into a 50 ml one neck flask, 20 ml Millipore water was also added, and the mixture was stirred for 30 minutes at room temperature. Now 1.2 g sodium periodate was added, and the mixture was allowed to react for two hours while protected from light. Then 1 ml ethylene glycol was added, and the reaction mixture was stirred for another 30 minutes. In the next step, 2 ml 2-(diisopropylamino)-ethylamine was added, and the mixture was stirred for four hours. After the completion of the coupling, 400 mg sodium cyanoborhydride was adjoined, and the reaction was continued over night with stirring. Then the reaction mixture was evaporated to dryness, and the dried product was used for the various applications described herein.

Example 2

Real Time PCR Performed in Copolymer Coated Plates

Sample Preparation (Generic Protocol)
1. Dispense 100 μl of Lysis buffer into each well of the uncoated strips.
2. Add 10 μl of blood sample to each well and mix by pipetting up and down 15 times.
3. Incubate the strips at room temperature for 15 minutes.
4. Aspirate as much liquid as possible using a pipette tip connected to vacuum.
5. Dispense 120 μl of Wash Solution into the appropriate wells.
6. Aspirate as much liquid as possible.
7. Add 25 μl of PCR Mastermix and carry out quantitative PCR (qPCR).

Lysis Buffer

KS19-EL: a mixture of poly (styrene-co-maleic anhydride) covalent coupling with DIPAEA (copolymer "KS19" [10 mg/ml]) and QIAGEN Buffer EL (Erythrocyte Lysis containing 155 mM $NH_4Cl$ and 10 mM $KHCO_3$). The volume ratios of KS19 to Buffer EL may be between 1:1 and 1:2.5.

KS19-RBCL: a 1:1 (volume:volume) mixture of the polymer "KS19" (10 mg/ml) and Gentra's Red Blood Cell Lysis Buffer RBCL (Gentra, Minneapolis, Minn.).

Wash Solutions

TE (10 mM Tris/Cl pH 8.0; 1 mM EDTA), TE with 0.05% Nonidet P40 (NP40), or deionized Water.

Experimental Results

First Experiment

In this experiment, the lysis of blood samples and binding of nucleic acid molecules in the samples to PCR plates were performed as described above. FIG. 1 represents the results of the quantitative real time PCR that amplified a chromosomal gene encoding beta-actin. The y-axis displays the "ng" (nanogram) of detected amplified DNA, and the X-axis shows different preparation setups using different lysis buffers. The most left column represents nucleic acid amplification using KS19-EL as the lysis buffer and uncoated plates according to the protocol described above with the exception that distilled water was used for washing, whereas all the other columns represent nucleic acid amplification using KS19 pre-coated plates and various lysis buffers without copolymer.

In summary, the yields of nucleic acid amplification using KS19-EL as lysis buffer and plates that were not pre-coated were similar to, or even slightly better than, those using copolymer pre-coated plates and various lysis buffers without copolymer.

Reproduction for Confirmation

Figure 2:
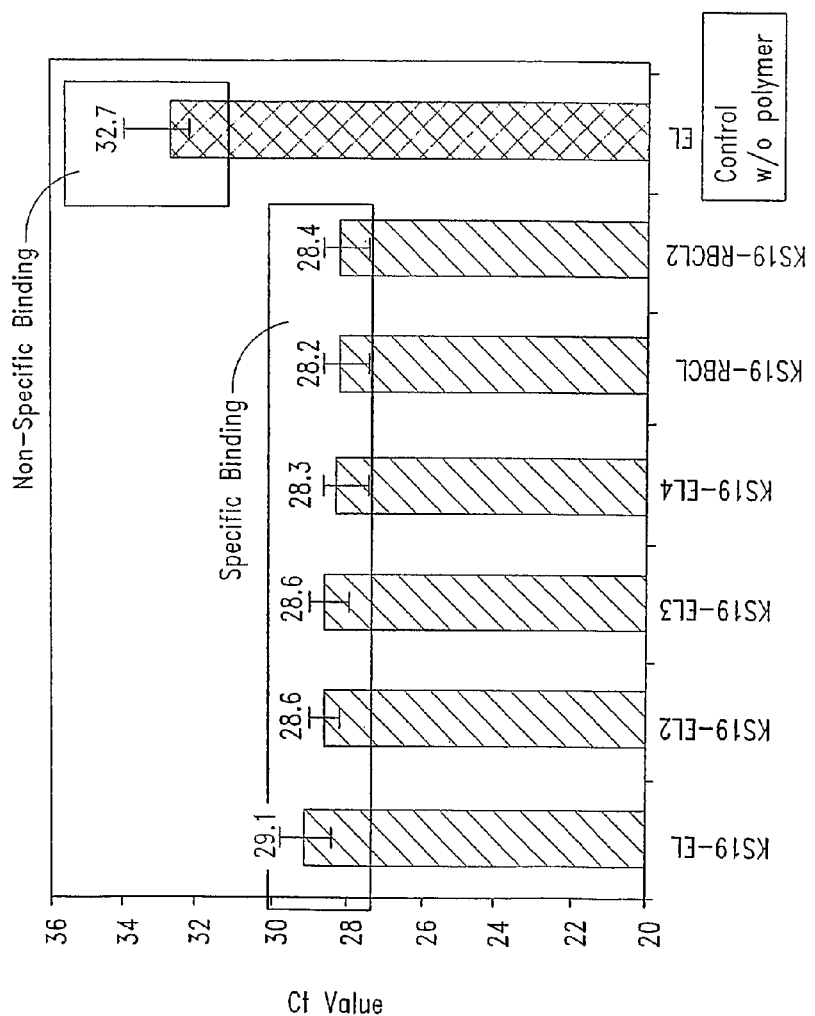
FIG. 2 is a bar graph showing binding specificity using various copolymer KS19-containing lysis buffers. The most right column indicates the results using only EL without KS19 as the lysis buffer, which serves as a control. The y-axis displays mean Ct values of real time PCR. The x-axis indicates various lysis buffers.

In this experiment, the previous results were confirmed. In addition, the lysis buffer was modified and a control showing the nucleic acid specificity was implemented. For control, lysis buffer EL was diluted 1:2 with distilled water, therefore the difference between the first column and the last column in FIG. 2 was just the presence of the KS19 polymer. The Y-axis of FIG. 2 shows the mean "Ct" value of the real time PCR, whereas the X-axis indicates various lysis buffers-copolymer combinations by diluting KS19 polymer with Buffer EL or Buffer RBCL. KS19-EL, KS19-EL2, KS19-EL3, and KS19-EL4 refer to 1:2, 1:2.5, 1:3, and 1:3.5 dilutions of KS19 with Buffer EL, respectively; whereas KS19-RBCL and KS19-RBCL2 refer to 1:2 and 1:3 dilutions of KS19 with Buffer RBCL, respectively. The difference between the Ct values of the first column and the last column is more than 3.3. This means that the presence of KS19 in the lysis buffer leads to a 10-fold improved detection of the genomic DNA in qPCR (PCR leads to exponential multiplication of the number of amplified fragments; $2^{3.3}=10$).

The results also show that the classical erythrocyte lysis buffer (EL) combined with KS19 allows for the most sensitive nucleic acid detection. Thus, it may be deduced that most KS19 polymer molecules bound nucleic acid-containing cellular organelles (i.e., nuclei and mitochondria) released by the erythrocyte lysis buffer, and that these organelles were immobilized to the vessel walls together with the polymer.

Experiments Focusing on Optimization

Figure 3:
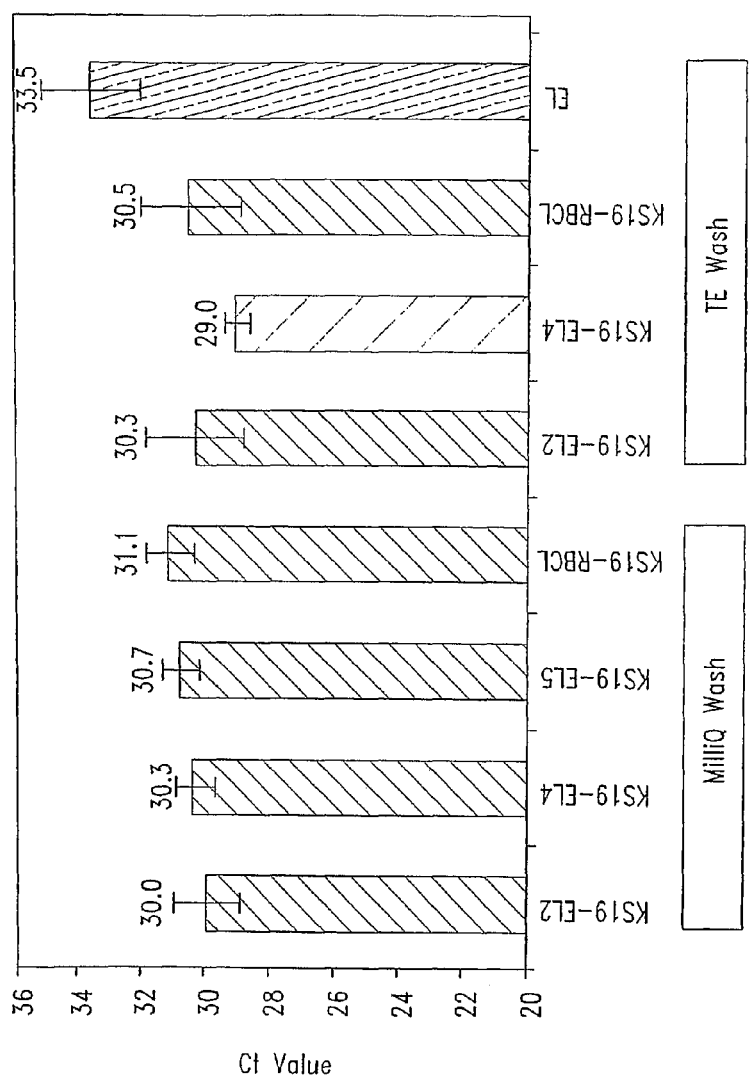
FIG. 3 is a bar graph showing real time PCR using various copolymer KS19-containing lysis buffers in combination with two wash buffers (MilliQ wash and TE wash). The most right column indicates the results using only EL without KS19 as the lysis buffer, which serves as a control. The y-axis displays mean Ct values of real time PCR. The x-axis indicates various lysis buffers.

By changing the wash buffer from MilliQ water to TE buffer, the performance of the protocol was further improved. This led to a Ct difference between PCR using KS19-EL and EL to be more than 4.5 (FIG. 3). This experiment showed that the use of KS19-EL could detect 2.1 ng genomic DNA via qPCR, meaning that the performance was improved by more than a factor of five.

Figure 4:
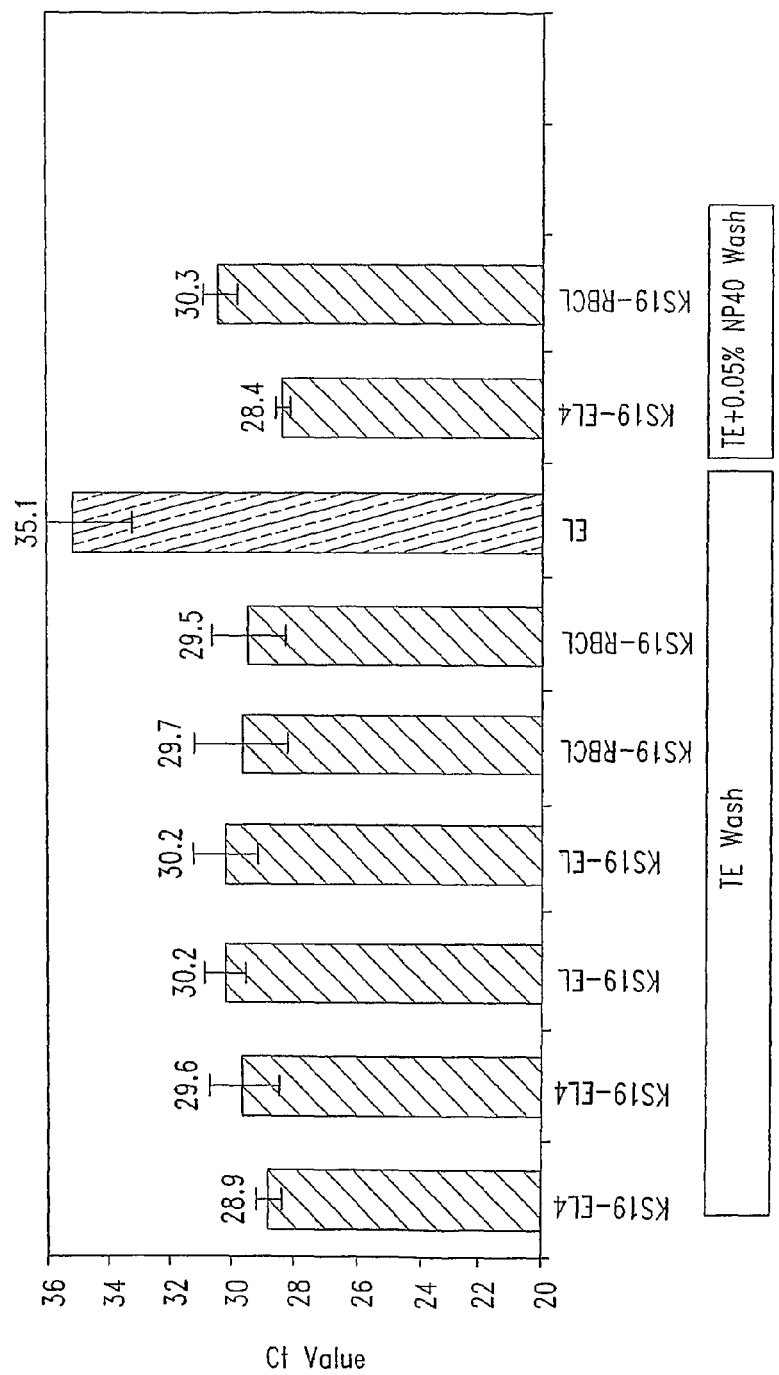
FIG. 4 is a bar graph showing real time PCR using various copolymer KS19-containing lysis buffers in combination with two wash buffers (TE Wash and TE+0.05% NP40 Wash). The most right column indicates the results using only EL without KS19 as the lysis buffer, which serves as a control. The y-axis displays mean Ct values of real time PCR. The x-axis indicates various lysis buffers.

All the results shown above were obtained by the use of a MJ Opticon 2 Real Time Cycler and suitable PCR consumables (8-well Strips). Similar experiments were also performed using an Applied Biosystems TaqMan System 7700 and ABI Optical Tubes and obtained results comparable to those using a MJ Opticon 2 Real Time Cycler (FIG. 4). In addition, the performance was improved further by using TE with 0.05% NP40 as the washing buffer, which was able to detect 1.6 ng of genomic DNA.

All of the above U.S. patents, U.S. patent application publications, U.S. patent applications, foreign patents, foreign patent applications and non-patent publications referred to in this specification and/or listed in the Application Data Sheet, are incorporated herein by reference, in their entirety.

From the foregoing it will be appreciated that, although specific embodiments of the invention have been described herein for purposes of illustration, various modifications may be made without deviating from the spirit and scope of the invention. Accordingly, the invention is not limited except as by the appended claims.

The invention claimed is:

1. A composition for nucleic acid immobilization and analysis, comprising:
   (1) a nucleic acid-containing biological sample, and
   (2) a lysis buffer comprising a synthetic copolymer, wherein the synthetic copolymer comprises a plurality of a first hydrophobic monomer, a plurality of a second monomer, and a plurality of an amino group-containing component, wherein
      (i) the first hydrophobic monomer is (a) styrene or (b) an alkene or alkapolyene having 2 to 8 carbon atoms,
      (ii) the second monomer provides at least one functionality to which the amino group-containing component is directly or indirectly covalently linked, wherein the second monomer is selected from the group consisting of maleic anhydride, acrylic acid, methacrylic acid, 4-hydroxy-styrene, and 4-vinyl-benzaldehyde, and
      (iii) the amino group-containing component is directly or indirectly covalently linked to the second monomer, wherein the amino group-containing component is selected from the group consisting of 2-(diisopropylamino)-ethylamine, N,N-diethyldiethylenetriamine, 1-(2-aminoethyl)pyrrolidine, 1-amino-4-methylpiperazine, N,N,2,2,-tetramethyl-1,3,-propanediamine, 3-(dibutylamine)propylamine, Girard's reagent T, choline chloride, 2-(2-diethylaminoethylamino)-ethanol, 2-{[2-(dimethylamino)ethyl]methylamino}ethanol, 1,3-bis-(diethylamino)-2-propanol, a-(diisopropylamino)ethanol, 2-[2-(dimethylamino)ethoxy]ethanol, 4-diisobytylamino-1-butanol, 6-dipropylamino-1-hexanol, and diethanolamine, and
   wherein the synthetic copolymer is capable of binding to a hydrophobic surface and a nucleic acid.

2. A method for extracting nucleic acid from a nucleic acid-containing biological sample comprising mixing a nucleic acid-containing biological sample with a lysis buffer to form the composition of claim 1.

3. A method for amplifying nucleic acid comprising:
   (i) combining a nucleic acid-containing biological sample with a lysis buffer to form the composition of claim 1;
   (ii) applying the composition of step (i) to a hydrophobic surface so that the nucleic acid in the biological sample is immobilized on the hydrophobic surface via the copolymer in the lysis buffer; and
   (iii) performing nucleic acid amplification using the nucleic acid immobilized on the hydrophobic surface as a template.

4. The method of claim 3 further comprising washing the hydrophobic surface before step (iii).

5. The composition of claim 1, wherein the first hydrophobic monomer is an alkene or alkapolyene having 2 to 8 carbon atoms.

6. The composition of claim 1 wherein the second monomer is maleic anhydride.

7. The composition of claim 1 wherein the second monomer is 4-hydroxy-styrene.

8. The composition of claim 1 wherein the amino group-containing component is directly covalently linked to the second monomer.

9. The composition of claim 1 wherein the amino group-containing component is indirectly covalently linked to the second monomer via a spacer portion.

10. The composition of claim 9 wherein the spacer portion is derived from a spacer-forming molecule selected from the group consisting of lactonolactone, unmodified and chemically modified poly(ethylene glycol) with the general formula $HO-(C_2H_4O)_n-H$ wherein n is 1 to 20,000, unmodified and chemically modified polypropylene glycol) with the general formula $HO-(C_3H_6O)_m-H$ wherein m is 1 to 20,000, glycerol diglycidylether, glycerol-propoxylate triglycerolether, and poly(meth)acrylic acid.

11. The composition of claim 1 wherein the synthetic copolymer is an amino-modified poly(styrene-co-maleic anhydride) having about 7% to about 50% (weight percentage) maleic anhydride.

12. The composition of claim 1 wherein the synthetic copolymer is an amino-modified poly(isoprene-graft-maleic anhydride) having about 7% to 50% of maleic anhydride.

13. The composition of claim 1 wherein the synthetic copolymer is an amino-modified poly(methylvinylether-alt-maleic anhydride) with about 50% of maleic anhydride.

14. The composition of claim 1 wherein the synthetic copolymer is an amino-modified stearyl acrylate-glycidyl methacrylate copolymer.

15. The composition of claim 1 wherein the synthetic copolymer is an amino-modified poly(styrene-glycidyl methacrylate) copolymer.

16. The composition of claim 1 wherein the synthetic copolymer is selected from the group consisting of an amine-modified poly(styrene-co-maleic anhydride), an amine-modified poly(isoprene-graft-maleic anhydride), an amine-modified poly(methyvinyllether-alt-maleic anhydride), an amine-modified steary acrylate-glycidyl methacrylate copolymer, and an amine-modified polystyrene-glycidyl methacrylate copolymer.

17. The composition of claim 1, wherein the nucleic acid-containing sample is blood.

18. The composition of claim 1, wherein the nucleic acid-containing sample is body fluid or cultured cells.

19. The method of claim 2, wherein the nucleic acid-containing sample is blood.

20. The method of claim 2, wherein the nucleic acid-containing sample is body fluid or cultured cells.

21. The method of claim 3, wherein the nucleic acid-containing sample is blood.

22. The method of claim 3, wherein the nucleic acid-containing sample is body fluid or cultured cells.

23. The composition of claim 1, wherein the first hydrophobic monomer is styrene.

24. The composition of claim 5, wherein the alkene or alkapolyene having 2 to 8 carbon atoms is an alkene having 2 to 8 carbon atoms.

25. The composition of claim 24, wherein the alkene having 2 to 8 carbon atoms is ethylene or propylene.

26. The composition of claim 5, wherein the alkene or alkapolyene having 2 to 8 carbon atoms is an alkapolyene having 2 to 8 carbon atoms.

27. The composition of claim 26, wherein the alkapolyene having 2 to 8 carbon atoms is butadiene.

28. The composition of claim 1, wherein the amino group-containing component is 2-(diisopropylamino)-ethylamine.

29. The method of claim 2, wherein the amino group-containing component is 2-(diisopropylamino)-ethylamine.

30. The method of claim 3, wherein the amino group-containing component is 2-(diisopropylamino)-ethylamine.

31. The composition of claim 1, wherein the second monomer is methacrylic acid.

* * * * *

UNITED STATES PATENT AND TRADEMARK OFFICE
CERTIFICATE OF CORRECTION

PATENT NO.         : 8,778,842 B2                         Page 1 of 1
APPLICATION NO.    : 11/883071
DATED              : July 15, 2014
INVENTOR(S)        : Ralf Himmelreich et al.

It is certified that error appears in the above-identified patent and that said Letters Patent is hereby corrected as shown below:

In the claims

Column 13, Lines 37-38:
"wherein the synthetic copolymer is capable of binding to a hydrophobic surface and a nucleic acid." should read, --wherein the synthetic copolymer is capable of binding to a hydrophobic surface and the nucleic acid in the biological sample.--.

Column 13, Lines 61-62:
"7. The composition of claim 1 wherein the second monomer is 4-hydroxy-styrene." should read, --7. The composition of claim 1 wherein the second monomer is 4-hydroxy-styrene or 4-vinyl-bezaldehyde.--.

Column 14, Line 6:
"chemically modified polypropylene glycol) with the general formula" should read, --chemically modified poly(propylene glycol) with the general formula--.

Signed and Sealed this
Twenty-second Day of March, 2016

Michelle K. Lee
*Director of the United States Patent and Trademark Office*